(12) United States Patent
Tucker et al.

(10) Patent No.: US 8,883,412 B2
(45) Date of Patent: Nov. 11, 2014

(54) SIZE STANDARDS FOR USE IN NUCLEIC ACID ANALYSIS

(75) Inventors: Valerie Carol Tucker, Birmingham (GB); Pieris Koumi, Birmingham (GB); Andrew John Hopwood, Birmingham (GB); Keith Elliot, Birmingham (GB)

(73) Assignee: Qiagen GmbH, Hilden (DE)

( * ) Notice: Subject to any disclaimer, the term of this patent is extended or adjusted under 35 U.S.C. 154(b) by 398 days.

(21) Appl. No.: 13/000,597

(22) PCT Filed: Jun. 29, 2009

(86) PCT No.: PCT/GB2009/001611
§ 371 (c)(1),
(2), (4) Date: Sep. 29, 2011

(87) PCT Pub. No.: WO2009/156741
PCT Pub. Date: Dec. 30, 2009

(65) Prior Publication Data
US 2012/0015355 A1    Jan. 19, 2012

(30) Foreign Application Priority Data
Jun. 27, 2008 (GB) .................................. 0811796.2

(51) Int. Cl.
*C12Q 1/68* (2006.01)
*C07H 21/00* (2006.01)
*C07H 21/02* (2006.01)
*C07H 21/04* (2006.01)
*C12P 19/34* (2006.01)

(52) U.S. Cl.
CPC ........................................ *C12Q 1/68* (2013.01)
USPC ......... 435/6.1; 536/22.1; 536/23.1; 536/24.3; 435/91.2

(58) Field of Classification Search
CPC ......... C12Q 1/68; C12Q 1/6827; C07H 21/00
USPC .................................. 435/6.1, 91.2; 536/22.1
See application file for complete search history.

(56) References Cited

U.S. PATENT DOCUMENTS

| | | | |
|---|---|---|---|
| 5,599,666 A | | 2/1997 | Schumm et al. |
| 5,962,249 A | * | 10/1999 | Benton et al. .................. 435/29 |
| 7,087,380 B2 | * | 8/2006 | Griffiths et al. .............. 435/6.11 |
| 7,662,594 B2 | * | 2/2010 | Kong et al. .................. 435/91.2 |

FOREIGN PATENT DOCUMENTS

| | | |
|---|---|---|
| EP | 0 887 426 B1 | 12/2006 |
| WO | WO 01/92575 A1 | 12/2001 |
| WO | WO 2004/033621 A2 | 4/2004 |
| WO | WO 2009/059049 A1 | 5/2009 |

OTHER PUBLICATIONS

Stratagene Catalog p. 39 (1988).*
Schmalzing et al. ,DNA typing in thirty seconds with a microfabricated device PNAS 94 :10,273 (1997).*
Wang et al., High-resolution capillary array electrophoretic sizing of multiplexed short tandem repeat loci using energy-transfer fluorescent primers. Electrophoresis 17 :1485 (1996).*
Ahern, H. The Scientist 9 (15) :20 pp. 7 of 7 (1995).*
Lins et al.,Multiplex Sets for the Amplification of Polymorphic Short Tandem Repeat Loci—Silver Stain and Fluorescence Detection. Biotechniques 20 (5) :882 (1996).*
STR Fact Sheet—D2S1338 found online on May 16, 2014.*
STR Fact Sheet—D1S1656 found online on May 16, 2014.*
STR Fact Sheet—D8S1179 found online on May 16, 2014.*
STR Fact Sheet—D2S441 found online on May 16, 2014.*
STR Fact Sheet—D12S391 found online on May 16, 2014.*
STR Fact Sheet—TPOX found online on May 16, 2014.*
STR Fact Sheet—D13S317 found online on May 16, 2014.*
STR Fact Sheet—SE33 found online on May 16, 2014.*
STR Fact Sheet—D10S1248 found online on May 16, 2014.*
Low Molecular Weight DNA Ladder , found online on May 16, 2014.*
Butler et al., "Short tandem repeat typing technologies used in human identity testing," *BioTechniques* (2007) 43 (4): II-V. XP008100506.
Form PCT/ISA/210 for corresponding International Application PCT/GB2009/001611.
Form PCT/ISA/220 for corresponding International Application PCT/GB2009/001611.
Form PCT/ISA/237 for corresponding International Application PCT/GB2009/001611.
Alshamali et al., "STR population diversity in nine ethnic populations living in Dubai," *Forensic Science International* (2005) 152: 267-279.
Barber et al., "Structural variation in the alleles of a short tandem repeat system at the human alpha fibrinogen locus," *Int. J. Legal Med.* (1996) 108: 180-185.
Barber et al., "Structural variation of novel alleles at the Hum vWA and Hum FES/FPS short tandem repeat loci," *Int. J. Legal Med.* (1995) 108: 31-35.
Brinkmann, B., "Population genetic comparisons among eight populations using allele frequency and sequence data from three microsatellite loci," *Eur. J. Hum. Genet.* (1996) 4: 175-182.
Budowle et al., "CODIS STR loci data from 41 sample populations," *J. Forensic Sci.* (2001) 46 (3): 453-489.
Cruz et al., "vWA STR locus structure and variability," *International Congress Series* (2004) 1261: 248-250.

(Continued)

*Primary Examiner* — Ethan Whisenant
(74) *Attorney, Agent, or Firm* — Fanelli Haag & Kilger PLLC (57) ABSTRACT

A size standard, kit includes a size standard, method of defining a size standard and method of analysis using a size standard. The size standard is intended to include size standard elements which have a size greater than and/or less than and/or different from the components of a sample which are to be sized. This means that the same characteristic unit, such as a dye, can be used to label the component and the size standard. A further characteristic unit, from amongst a limited number of such characteristic units is liberated from use only on size standards for use on components. The method is therefore particularly useful in multiplex amplification of STRs.

10 Claims, 3 Drawing Sheets

(56) References Cited

OTHER PUBLICATIONS

Decorte et al., "Allele frequency data for 19 short tandem repeats (PowerPlex® 16 and FFFl) in a Belgian population sample," *J. Forensic Sci.* (2006) 51 (2): 436-437.

Destro-Bisol et al., "Microsatellite variation in central Africa: An analysis of intrapopulational and interpopulational genetic diversity," *American Journal of Physical Anthropology* (2000) 112: 319-337.

Dupuy et al., "A dedicated internal standard in fragment length analysis of hyperpolymorphic short tandem repeats," *Forensic Science International* (1997) 207-227.

Gill et al., "A new method of STR interpretation using inferential logic—development of a criminal intelligence database," *Int. J. Legal Med.* (1996) 109: 14-22.

Gill et al., "Considerations from the European DNA profiling group (EDNAP) concerning STR nomenclature," *Forensic Science International* (1997) 87: 185-192.

Gill et al., "Report of the European DNA profiling group (EDNAP): An investigation of the complex STR loci D21S11 and HUMFIBRA (FGA)," *Forensic Science International* (1997) 86: 25-33.

Griffiths et al., "New reference allelic ladders to improve allelic designation in a multiplex STR system," *Int. J. Legal Med.* (1998) 111: 267-272.

Hochmeister et al., "Swiss population data on three tetrameric short tandem repeat loci—VWA, HUMTH01, and F13A1—derived using multiplex PCR and laser fluorescencedetection," *Int. J. Leg. Med.* (1994) 107: 34-36.

Kang et al., "Allele frequencies of 15 STR loci of Luoba ethnic group in Tibet (Southwestern China)," *Forensic Science International* (2005) 155: 219-221.

Kido et al., "Nine short tandem repeat loci analysis in aged semen stains using the AmpFLSTR Profiler Kit and description of a new vWA variant allele," *Legal Medicine* (2003) 5: 93-96.

Kimpton et al., "A further tetranucleotide repeat polymorphism in the vWF gene," *Human Molecular Genetics* (1992) 1 (4): 287.

Klintschar et al., "A study of the short tandem repeat systems HUMVWA and HUMTH01 in an Austrian population sample," *Int. J. Legal Med.* (1995) 107: 329-330.

Lincoln, PJ, "DNA recommendations—further report of the DNA Commission of the ISFH regarding the use of short tandem repeat systems," *Editorial/Forensic Science International* (1997) 87: 179-184.

Ma et al., "Han Chinese population data for ten STR loci in Changsha, China," *J Forensic Sci.* Mar. 2002; 47 (2): 404-5.

Moller et al., "Different types of structural variation in STRs: HumFES/FPS, HumVWA and HumD21S11," *Int. J. Leg. Med.* (1994) 106: 319-323.

Pandu et al., "Genetic profile of nine STR loci among Goud and Padmashali populations of Andhra Pradesh, India," *Forensic Science International* (2006) 157: 201-205.

Roy et al., "Autosomal STR variations in three endogamous populations of West Bengal, India," *Legal Medicine* (2008) 10: 326-332.

Sprecher et al., "General approach to analysis of polymorphic short tandem repeat loci," *BioTechniques* (1996) 20: 266-276.

Urquhart et al., "Variation in short tandem repeat sequences—a survey of twelve microsatellite loci for use as forensic identification markers," *Int. J. Leg. Med.* (1994) 107: 13-20.

Urquhart et al., "Highly discriminating heptaplex short tandem repeat PCR system for forensic identification," *BioTechniques* (1995) 18 (1): 116-121.

Griffiths, et al., "New reference allelic ladders to improve allelic designation in a multiplex STR system", Int. J. Legal Med. (1998) 111:267-272.

Wang, et al., "High-resolution capillary array electrophoretic sizing of multiplexed short tandem repeat loci using energy-transfer flourescent primers", Electrophoresis (1996) 17, 1485-1490.

\* cited by examiner

FIG. 2

FIG. 4

SIZE STANDARDS FOR USE IN NUCLEIC ACID ANALYSIS

This application is a National Stage Application of PCT/GB2009/001611, filed Jun. 29, 2009, which claims benefit of Ser. No. 0811796.2, filed Jun. 27, 2008 in the United Kingdom and which applications are incorporated herein by reference. To the extent appropriate, a claim of priority is made to each of the above disclosed applications.

This invention concerns improvements in and relating to analysis, particularly of nucleic acid containing samples.

Existing approaches to the analysis of nucleic acid containing samples, for instance forensic DNA samples, using a size standard to provide reference points from which the sizes of the elements in the analysis sample can be determined. The size standard is formed of a series of size standard elements. The size standard elements of a size standard are labelled with a label, the identity of the label being different to the labels used for the unknown identities the sample is being tested for.

The number of labels available is restricted and hence there is a restriction on the number of loci which can be considered in one analysis.

It is amongst the potential objects of the invention to provide an approach which increases the number of loci which can be considered in one analysis of an analysis sample and/or to increase the number of analysis samples which can be considered in a unit of time.

According to a first aspect of the invention we provide a size standard, the size standard being for use in determining the size or sizes of a component in a nucleic acid containing sample, the component having one or more known possible sizes, the known possible sizes having a range of sizes defined by the largest and smallest known possible size, the size standard including one or more size standard elements, wherein the size of one or more of those size standard elements is selected to be:
a) larger than the largest of the known possible sizes for the component; or
b) smaller than the smallest of the known possible sizes for the component; or
c) different from any of the sizes of the known possible sizes for the component.

The component may be a part of the nucleic acid containing sample which is amplified. The component may be a part of the nucleic acid containing sample which has a location which has one or more sizes from a set of one or more possible sizes. The component may be a locus. The component may be a location for which the size is variable, for instance a locus. The component may be one of the following loci: VWA, D16S539, D2S1338, D8S1179, D21S11, D18S51, D19S433, TH01, FGA, D3S1358, D10S1248, D22S1045, D2S441, D1S1656, D12S391, TPDX, D14S1434, CSF1PO, D5S818, D7S820, D13S317 or SE33. The use for determining the size or sizes of a component may consider one or more different components. The use may use two or more of these loci, preferably five or more of these loci, more preferably eight or more of these loci and ideally eleven or more of these loci. One or more of these loci may be used alongside one or more other loci.

The size or sizes of the component may be the size or sizes for that sample out of the set of one or more possible sizes. The size or sizes are preferably allele size or sizes.

The one or more known possible sizes for a component may be a summation of the published knowledge on the component at the time the size standard is manufactured. The one or more known possible sizes for a component may be a summation of the published knowledge on the component at 15 Jun. 2009. The one or more known possible sizes may be a set of sizes for that component. The set of sizes for one or more of the components listed in Table 1 may be as defined in Table 1, preferably according to the nomenclature of Gill et al., *Considerations from the European DNA profiling group (EDNAP) concerning STR nomenclature, Forensic Science International*, 87 (1997) 185-192) and/or potentially with the addition of an additional size part corresponding to the flanking sequence at the 5' side and/or 3' side of the short tandem repeat sequence introduced during amplification by the primers used.

In a preferred embodiment, we provide a size standard, the size standard being for use in determining the allele size or sizes at a locus in a nucleic acid containing sample, the locus having one or more known possible allele sizes, the known possible allele sizes having a range of sizes defined by the largest and smallest known possible size alleles, the size standard including one or more size standard elements, wherein the size of one or more of those size standard elements is selected to be: larger than the largest of the known possible alleles; or smaller than the smallest of the known possible alleles; or different from any of the sizes of the known possible alleles. Preferably the size of one or more of the size standard elements is selected to be larger than the largest of the known possible alleles and/or smaller than the smallest of the known possible alleles and/or different from any of the sizes of the known possible alleles, taking into account any additional sequence parts which are additional to the size variable parts of the allele(s), for instance the flanking sequence included at the 5' and/or 3' end of the amplified component(s) of the sample.

The component and/or size or sizes of component may include a characteristic unit, such as a label, for instance a dye. The same characteristic unit may be used for all size or sizes of the same component, particularly where the component is a locus. The same characteristic unit may be used for the size standard and/or one or more, preferably all, of the standard size elements used in determining the size or sizes for a component as are included in the size or sizes of component for that component.

The same characteristic unit may be used for two or more components, particularly where the range of sizes defined by the largest and smallest known possible sizes for those two or more components do not overlap in size. The same characteristic unit may be used for the size standard and/or one or more, preferably all, of the standard size elements used in determining the size or sizes for all components using the same characteristic unit.

Preferably at least five different components are provided which will each incorporate a different characteristic unit from each other. One, two, three or more different components may be provided which incorporate the same characteristic unit for each of five, potentially more, different characteristic units.

Preferably all channels and/or capillaries in the analysis instrument are used to analyse samples with unknown nucleic acid.

The size standard may include one or more size standard elements formed of nucleic acids.

Preferably the size standard includes one or more size standard elements, wherein the size of one or more of those size standard elements is selected to be: larger than the largest of the known possible sizes for each component including the same characteristic unit as the size standard; or smaller than the smallest of the known possible sizes for each component including the same characteristic unit as the size standard; or different from any of the sizes of the known possible sizes for each component including the same characteristic unit as the size standard. Preferably the size standard includes one or more size standard elements, wherein the size of one or more of those size standard elements is selected to be: larger than the largest of the known possible allele sizes for each locus including the same characteristic unit as the size standard; or smaller than the smallest of the known possible allele sizes for each locus including the same characteristic unit as the size standard; or different from any of the allele sizes of the known possible allele sizes for each locus including the same characteristic unit as the size standard. Preferably the size of one or more of the size standard elements is selected to be larger than the largest of the known possible alleles and/or smaller than the smallest of the known possible alleles and/or different from any of the sizes of the known possible alleles, taking into account any additional sequence parts which are additional to the size variable parts of the allele(s), for instance the flanking sequence included at the 5' and/or 3' end of the amplified component(s) of the sample.

The size standard may include one or more size standard elements, wherein the size of one or more of those size standard elements is not selected to be: larger than the largest of the known possible sizes for one or more, possibly each, component including a different characteristic unit to the size standard; or smaller than the smallest of the known possible sizes for one or more, possibly each, component including a different characteristic unit to the size standard; or different from any of the sizes of the known possible sizes for one or more, possibly each, component including a different characteristic unit to the size standard.

One or more of the size standard elements may be of a size which is less than the smallest size of the known possible sizes for one locus and greater than the largest size of the known possible sizes of another locus. Preferably the smallest size of the one locus is greater in size than the largest size of another locus. Preferably the one locus and the another locus use the same characteristic unit. Where three or more loci are considered using the same characteristic unit, preferably one or more of the size standard elements may be of a size which is less than the smallest size of the known possible sizes for one locus and greater than the largest size of the known possible sizes of another locus, in respect of each pair of loci whose known possible size ranges are adjoining.

Where two or more loci are considered using the same characteristic unit, preferably one or more size standard elements are provided which have a size smaller than the smallest size of the known possible sizes of the two or more loci. Preferably at least two such standard size elements are so provided.

Where two or more loci are considered using the same characteristic unit, preferably one or more size standard elements are provided which have a size larger than the largest size of the known possible sizes of the two or more loci. Preferably at least two such standard size elements are so provided.

Preferably two or more loci are considered using the same characteristic unit in respect of each of two or more different characteristic units. Preferably for each of the two or more different characteristic units, one or two or more size standard elements are provided which have a size smaller than the smallest size of the known possible sizes of the two or more loci and/or one or two or more size standard elements are provided which have a size larger than the largest size of the known possible sizes of the two or more loci. Preferably two or more loci are considered using the same characteristic unit in respect of each of five different characteristic units. Preferably for each of the five different characteristic units, one or two or more size standard elements are provided which have a size smaller than the smallest size of the known possible sizes of the two or more loci and/or one or two or more size standard elements are provided which have a size larger than the largest size of the known possible sizes of the two or more loci.

One or two or more of the size standard elements may be of a size which is less than one of the known possible sizes for a locus and is greater than one of the known possible sizes of that locus. One or two or more of the size standard elements may be of a size which fits in a gap within the known possible sizes for a locus.

The size standard may include a set of one or more size standard elements provided with a characteristic unit and one or more further sets of one or more size standard elements provided with a different characteristic unit. The size standard may be a composite formed of two or more sets of one or more size standard elements, the sets being provided with different characteristic units. A set may include two or more, preferably 3 or more, more preferably 5 or more, and ideally seven or more size standard elements. The number of size standard elements may be the same in each set or may be different. Four, five, six, seven or more sets of size standard elements may be provided, each with a different characteristic unit.

The size standard may include at least 10 size standard elements, preferably at least 15, more preferably at least 20 and ideally at least 25. The size standard may include 36 size standard elements or less and may have 30 size standard elements or less.

Where two or more components are considered, then one or more size standard elements which are the same size may be used for two or more of the two or more components considered. Where two or more components are considered, then one or more size standard elements which are the same size may be used for all of the two or more components considered.

One or more of size standard elements which are the same size as each other may be larger than the largest of the known possible sizes for two or more of those two or more components being considered. All of the size standard elements which are the same size as each other may be larger than the largest of the known possible sizes for all of the two or more components being considered.

One or more of size standard elements which are the same size as each other may be smaller than the smallest of the known possible sizes for two or more of those two or more components being considered. All of the size standard elements which are the same size as each other may be smaller than the smallest of the known possible sizes for all of the two or more components being considered.

One or more of size standard elements which are the same size as each other may be different in size from all of the known possible sizes for two or more of those two or more components being considered. All of the size standard elements which are the same size as each other may be different in size from all of the known possible sizes for all of the two or more components being considered.

A size standard element may be provided which is at least 1 base pair smaller in size than the smallest known possible allele the size standard is being used to size. Preferably the size standard element is at least 2 base pairs smaller, more preferably at least 3 base pairs smaller and potentially 4 or more base pairs smaller. A size standard element may be provided which is at least 0.1 designations smaller in size than the smallest known possible allele the size standard is being used to size. Preferably the size standard element is at least 0.2 designations smaller, more preferably at least 0.3 designations smaller and potentially 1 or more designations smaller.

A size standard element may be provided which is at least 1 base pair larger in size than the largest known possible allele the size standard is being used to size. Preferably the size standard element is at least 2 base pairs larger, more preferably at least 3 base pairs larger and potentially 4 or more base pairs larger. A size standard element may be provided which is at least 0.1 designations larger in size than the largest known possible allele the size standard is being used to size. Preferably the size standard element is at least 0.2 designations larger, more preferably at least 0.3 designations larger and potentially 1 or more designations larger.

Where a size standard element is provided intermediate the size range of known possible alleles for one locus and the known possible size range for another locus, preferable the size standard element is provided to be at least 1 base pair larger in size than the largest allele of the range with the smaller sizes and at least 1 base pair smaller in size than the smallest allele of the range with the larger sizes. The size standard element may be at least 2 base pairs larger and at least 2 base pairs smaller respectively. The size standard element may be at least 3 base pairs larger and at least 3 base pairs smaller respectively. The size standard element may be at least 4 base pairs larger and at least 4 base pairs smaller respectively. Where a size standard element is provided intermediate the size range of known possible alleles for one locus and the known possible size range for another locus, preferable the size standard element is provided to be at least 0.1 designations larger in size than the largest allele of the range with the smaller sizes and at least 0.1 designations smaller in size than the smallest allele of the range with the larger sizes. The size standard element may be at least 0.2 designations larger and at least 0.2 designations smaller respectively. The size standard element may be at least 0.3 designations larger and at least 0.3 designations smaller respectively. The size standard element may be at least 1 designation larger and at least 1 designation smaller respectively.

The first aspect of the invention may include any of the features, options or possibilities set out elsewhere within this document, including in the second and/or third and/or fourth aspects of the invention. In particular, the term locus may be replaced by the term component and/or the term loci may be replaced by the term components, or vice-versa, in any of the statements contained herein.

According to a second aspect of the invention we provide a kit, the kit comprising:

a size standard, the size standard including the size standard being for use in determining the size or sizes of a component in a nucleic acid containing sample, the component having one or more known possible sizes, the known possible sizes having a range of sizes defined by the largest and smallest known possible size, the size standard including one or more size standard elements, wherein the size of one or more of those size standard elements is selected to be: a) larger than the largest of the known possible sizes for the component; or b) smaller than the smallest of the known possible sizes for the component; or c) different from any of the sizes of the known possible sizes for the component;

and one or more of the following components:
a) one or more primers;
b) one or more probes;
c) one or more characteristic units, such as labels or dyes;
d) one or more buffers;
e) one or more HCl solutions;
f) one or more EDTA solutions;
g) one or more gender markers, such as Amelogenin;
h) one or more allelic ladders;
i) one or more enzymes, such as Taq polymerase;
j) one or more reagents for use in PCR;
k) one or more deoxynucleotide triphosphates;
l) one or more solutions containing Mg and/or Mn ions;
m) one or more solutions containing K ions.

The second aspect of the invention may include any of the features, options or possibilities set out elsewhere within this document, including in the first and/or second and/or fourth aspects of the invention. In particular, the term locus may be replaced by the term component and/or the term loci may be replaced by the term components, or vice-versa, in any of the statements contained herein.

According to a third aspect of the invention we provide a method of analysing a nucleic acid containing sample to determine the size or sizes of a component of the sample, the component having one or more known possible sizes, the known possible sizes having a range defined by the largest and smallest known possible sizes, the method including:

introducing a size standard to at least a part of the sample, the size standard including one or more size standard elements;

performing a size based separation on at least a part of the sample;

determining the positions of the size standard elements detected;

using the size standard elements to determine the size or sizes of the component;

wherein the size of one or more of those size standard elements is selected to be:
 a) larger than the largest of the known possible sizes for the component; or
 b) smaller than the smallest of the known possible sizes for the component; or
 c) different from any of the sizes of the known possible sizes for the component.

The method may include one or more of the following steps: collecting a sample; preparing a sample for amplification; amplifying a sample, for instance using PCR; performing a size based separation using electrophoresis, for instance in a capillary or channel, particularly using a capillary gel electrophoresis instrument.

The method may include adding one or more of components a) to m) of the second aspect of the invention. The one or more components may be added during the preparing of the sample for amplification and/or during amplification and/or in preparation for the size based separation.

Preferably the method includes the analysis of the sample in at least 1 channel or capillary of an instrument. Preferably all the capillaries or channels used to analyse a sample are used to perform a size based separation on the sample. Preferably none of the capillaries or channels used to analyse a sample are used to perform a size based separation on only a size standard.

The method may determine the positions of the size standard elements using a laser. The laser may cause fluorescence of a characteristic unit of a size standard element, particularly a dye.

The determining of the positions of the size standard elements may include generating a data set including data components representing the position of fluorescence and level of fluorescence observed for each capillary in respect of at least each size standard element and preferably each size standard element and each size or sizes of the component, for instance allele or alleles of a locus. The data set may include one or two components for the allele size or sizes for each locus analysed where the source of the sample is from a single person. The data set may include one or more components for the allele size or sizes for each locus analysed where the source of the sample is from more than one person.

Before the size standard elements are used to determine the size or sizes of the component or components, the consistency of migration of the size standard and/or size standard elements during the size based separation may be checked.

The determining the positions of the size standard elements detected may provide an experimental position for one or more, preferably each, size standard element. The method may include prior knowledge of the theoretical position of the size standard elements after the size based separation has been performed.

The theoretical position of one or more size standard elements may be compared with the experimental position of one or more size standard elements. Preferably the experimental position and theoretical position for the same size standard element are so compared. The comparison may be a direct comparison of the theoretical position and experimental position for size standard element. The comparison may be a comparison based upon the experimental position of a size standard element relative to the experimental position of one or more other size standard elements, for instance when compared with the theoretical position of a size standard element relative to the theoretical position of one or more other size standard elements. One or two or more size standard elements whose size is less than the size standard element being checked may be used and/or one or two or more size standard elements whose size is greater than the size standard element being checked may be used. Preferably the size standard elements are those immediately less than and/or greater than in size to the size standard element being considered. Ideally the same size standard elements are considered in each such comparison.

A plot of the theoretical positions for two or more of the size standard elements may be compared for its fit with a plot of the experimental positions for two or more of the size standard elements. The plot may be of migration position against size. A statistical tool may be used to quantify the fit. If the fit is poorer than a threshold, the analysis may be stopped or discarded or subjected to a specific analysis approach. If the fit is better than a threshold, the analysis may be continued and/or used.

The method may include checking the consistency of migration for different characteristic units by comparing the experimental positions for a first size standard element and a second size standard element, the first and second size standard elements being the same size, but differing in terms of characteristic unit. A plurality of first sized size standard elements which differ from each other in size may be compared a plurality of second sized size standard elements which differ from each other in size, but correspond in size to one of the first size standards considered. First and second size standard elements may be provided which have a size greater than the largest known possible size for one or more, preferably all components. First and second size standard elements may be provided which have a size smaller than the smallest known possible size for one or more, preferably all components. First and second size standard elements may be provided which have a size intermediate to the largest known possible size for one or more, preferably all components and the smallest known possible size for one or more, preferably all components. The same first and second size standard elements may be used for two or more, and preferably all, the characteristic units used.

The size standard elements are used to determine the size or sizes of the component or components, if the consistency of migration of the size standard and/or size standard elements during the size based separation is acceptable.

The size standard elements may be used indirectly to determine the size or sizes of the component or components. The size standard elements may be used to determine the level of migration of one or more other known size elements. The size standard elements may be used to determine the position of one or more other known elements. The one or more other known size elements may be elements of an allelic ladder.

The size standard elements may be used to determine the size or sizes of the component or components by comparing the experimental position of the size or sizes of the component with the relationship of position to a size defined by the experimental positions of the size standard elements. The position may be converted to a size by this comparison. The relationship may be a corrected relationship to reflect differences in and/or the comparison of the experimental position and theoretical position of one or more of the size standard elements.

The size standard elements may be used directly to determine the size or sizes of the component or components.

The size elements may be used to determine the size or sizes of the component or components by comparing the experimental position of the size or sizes of the component with the relationship of position to size defined by the experimental positions of the size standard elements. The position may be converted to a size by this comparison. The relationship may be a corrected relationship to reflect differences in and/or the comparison of the experimental position and theoretical position of one or more of the size standard elements.

The size or sizes of the components may be stored electronically and/or displayed to a user, for instance electronically and/or in hard copy. The stored information may include the size and/or quantity of component detected, for instance as an associated level of fluorescence. The size or sizes of the components may be expressed in a further form, for instance as a genotype for the nucleic acid of the sample.

The fourth aspect of the invention may include any of the features, options or possibilities set out elsewhere within this document, including in the first and/or second and/or third aspects of the invention. In particular, the term locus may be replaced by the term component and/or the term loci may be replaced by the term components, or vice-versa, in any of the statements contained herein.

According to a fifth aspect of the invention we provide a method of defining a size standard and/or a method of production for a size standard, the size standard being for use in determining the size or sizes of a component in a nucleic acid containing sample, comprising:

1) establishing for the component, all of the possible sizes for the component at the date of defining of the method, the possible sizes defining the known possible sizes, the known possible size standards having a range of sizes defined by the largest and smallest known possible size, 2) subsequently, providing and/or producing a size standard, the size standard including one or more size standard elements, wherein the size of one or more of those size standard elements is selected to be:
   a) larger than the largest of the known possible sizes for the component; or
   b) smaller than the smallest of the known possible sizes for the component; or
   c) different from any of the sizes of the known possible sizes for the component.

The one or more known possible sizes for a component may be a summation of the published knowledge on the component at the time the size standard is manufactured and/or method of manufacture is defined and/or size standard form is defined. The one or more known possible sizes for a component may be a summation of the published knowledge on the component at 15 Jun. 2009. The one or more known possible sizes may be a set of sizes for that component. The set of sizes for one or more of the components listed in Table 1 may be as defined in Table 1, preferably according to the nomenclature of Gill et al., *Considerations from the European DNA profiling group (EDNAP) concerning STR nomenclature, Forensic Science International*, 87 (1997) 185-192) and/or potentially with the addition of an additional size part corresponding to the flanking sequence at the 5' side and/or 3' side of the short tandem repeat sequence introduced during amplification by the primers used.

The fifth aspect of the invention may include any of the features, options or possibilities set out elsewhere within this document, including in the first and/or second and/or third aspects of the invention. In particular, the term locus may be replaced by the term component and/or the term loci may be replaced by the term components, or vice-versa, in any of the statements contained herein.

Various embodiments of the invention will be described, by way of example only, and with reference to the accompanying drawings, in which.

For a variety of reasons, it is useful to be able to analyse nucleic acid containing samples, including samples containing DNA. Such analyses are useful in forensic science and medical situations, for instance.

The analysis is frequently concerned with considering the particular identities present at one or more identities capable of variation. An example of such an approach is the consideration of allele identity or identities present at a location, locus, known to be variable. The alleles vary in identity due to variations in their size in many cases, such as in STRs. The variations in size are caused by variations in the form of the short tandem repeat, STR, sequence at these loci. Typically, the STR sequence is formed of a series of 4 base repeats, with varying numbers of each of the repeats. However, other variations aside from the number and type of 4 base pair repeats present may occur. The variation in the number of repeat units present and/or other bases present gives rise to different size alleles. By considering the allele identity (for homozygous individuals) or allele identities (for heterozygous individuals) that are present for a number of different loci significant information can be obtained.

Whilst the invention is described in relation to STRs, it is applicable to any approach in which unknown identities are to be established. Such situations include the consideration of PCR products from VNTRs and RAPDs, for instance, where the size varies as well.

When an unknown sample from a single source is analysed, only one or two of these alleles will be present, for each locus.

To reveal the identities of the alleles in the analysis sample, capillary electrophoresis is used to separate the alleles based upon their size, after amplification of the sample using PCR. The result of the size based separation is that the alleles are at different positions within the gel of the capillary.

The different positions are rendered detectable by introducing labels to the alleles prior to the size based separation. The labels may be introduced during amplification. The labels fluoresce in response to laser light applied by the detecting instrument. The position on the capillary at which fluorescence is detected and the level of the fluorescence informs about the identity of the allele and the level at which it is present.

Instruments and labels are designed with reference to one another. A common intention is to provide a plurality of labels that are excited by the same wavelength of laser light, but which emit at wavelengths which are discrete from one another. In this way, a single laser can be used by the instrument, but separate detection of each label can be provided for.

This approach commonly limits the available labels to a total of 5 available for concurrent use in most cases, or six in a more recent development.

When investigating the identities of alleles in this way, the position within the capillary attribute to an emission must be accurately established. To do this, it is known to use a size standard in each capillary featuring an unknown sample and an allelic ladder in a separate capillary. The positions of the known size standard elements which make up the size standards can then be used as reference points for sizing the positions observed from the analysis of the samples having unknown alleles. This is done by comparing the size standard elements with the allelic ladder to establish the extent of migration of the allelic ladder. The positions of the alleles of the allelic ladder are thus defined. These known size alleles can then be used to designate the sizes of the unknown alleles in the sample being tested.

This approach uses one label for the size standard and its size standard elements and so leaves one less, for instance four, labels for the analysis samples and their unknown alleles. To gain sufficient information on the analysis samples and their alleles, a series of different loci which have variable identity alleles are considered. Where the sizes of the unknown alleles for different loci can overlap, a different label must be use for the different loci so that they can be distinguished. Otherwise, there is no way of telling which locus and which allele is involved.

This requirement, together with the requirement for the size standard to have its own label, limits the total number of loci that can be considered in one analysis.

Use of Synthetic Elements

The present invention provides a different approach to the manner and location used for the provision of the size standards.

The approach can be illustrated with respect to a specific locus which is being analysed for. For a specific locus, research and experience has revealed the extent of the observed alleles for that locus, together with the details of the individual alleles observed for that locus. Thus, for the locus HUMTH01, the extent of the alleles may range from 4 up to 13.3 (according to the accepted form of nomenclature Gill et al., *Considerations from the European DNA profiling group (EDNAP) concerning STR nomenclature, Forensic Science International*, 87 (1997) 185-192) and with that locus having individual alleles 4, 5, 6, 7, 8, 9, 9.3, 10, 11 and 13.3. The designation is based upon the number of 4 base unit repeats present; whole numbers representing whole 4 base repeats; 0.1, 0.2 and 0.3 representing 1, 2 and 3 base blocks, an incomplete repeat. This position is illustrated in FIG. 1 with a vertical line corresponding to the position of each of the possible alleles.

Figures 1, 3:
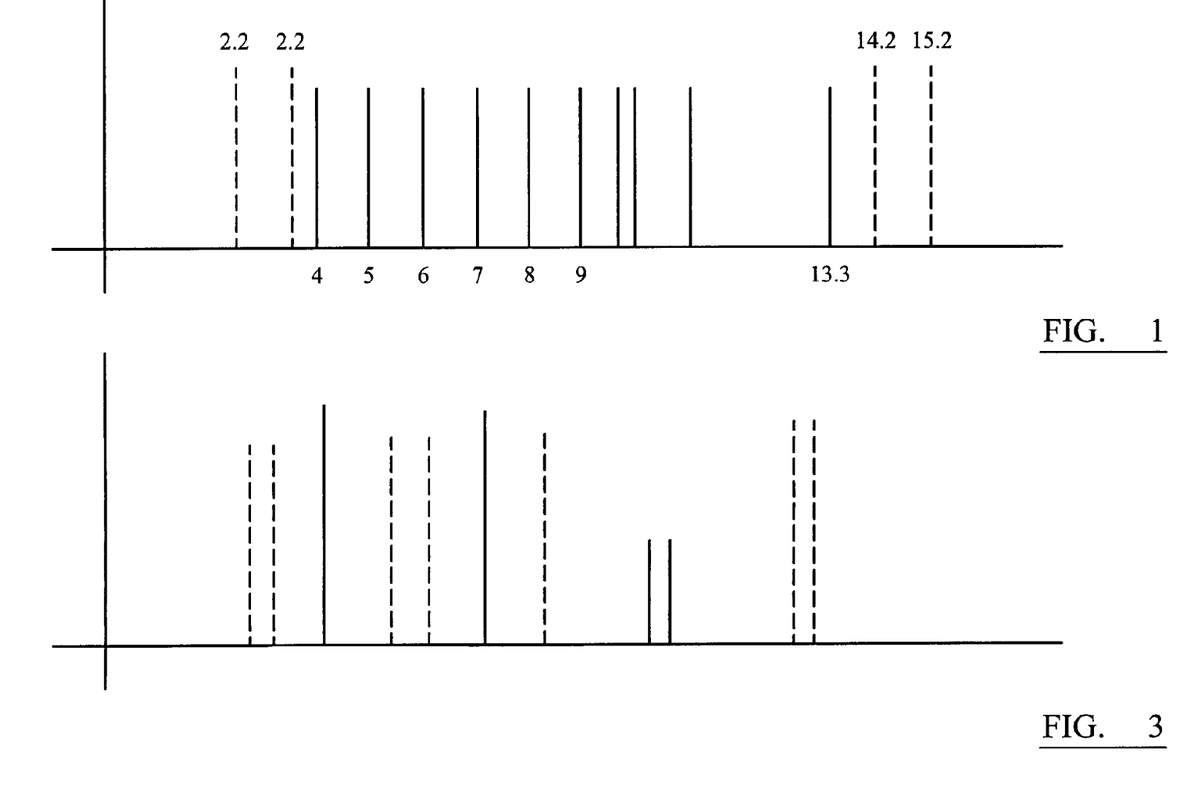
FIG. 1 is an illustration of the known alleles and the synthetic elements of the present invention for a locus.
FIG. 3 is an illustration of analysis results for the blue dye loci of FIG. 2, showing the synthetic element positions and positions for the unknown alleles of the sample.

As can be seen in FIG. 1, there are small gaps between the various alleles, a larger gap between alleles towards the upper end and gaps above and below the extreme value alleles. The inventions approach to the size standard makes use of these gaps.

A series of synthetic elements are provided in the size standard for sizing the alleles of a locus. These use the same dye or other label as is used to identify the alleles for that locus. Thus they will use the same label as the elements of the analysis sample in respect of that locus. The synthetic alleles are carefully constructed to be positioned in the gaps.

The gaps can be used in a wide variety of ways, with a particularly preferred form for use in considering a large number of loci simultaneously provided below.

As an illustration of the synthetic element use in a single locus case, in the example, synthetic alleles could be provided at sizes 2.2, 3.2, 14.2 and 15.2. These synthetic elements are shown in FIG. 1 as dotted vertical lines.

It is important that the synthetic elements do not coincide in size with any of the anticipated alleles of the unknown sample. Otherwise they could potentially obscure an allele present in the unknown sample or potentially give a false indication of an allele being present in the unknown sample. Thus the synthetic elements are distinct in terms of their position after the size based separation; electrophoresis.

Providing the size standard in this way means that the dye previously used for the size standard can be put to another use. The another use can, for instance, be to label the alleles of one or more further loci. This is beneficial as the number of dyes available is limited. The provision of further dyes is not simple as they need to be detectable by the instrument, behave in a consistent manner with the existing dyes and so on. The simultaneous analysis of more loci enables more information to be obtained without requiring separate analyses which take up further time and/or resources.

Table 1 defines the possible sizes for the listed loci, with those loci including many of relevance to forensic investigations. This data is consistent with that provided on the Short Tandem Repeat DNA Internet Database website operated through The NIST Office of Law Enforcement Standards provided by The National Institute for Justice on 15 Jun. 2009.

Figure 2:
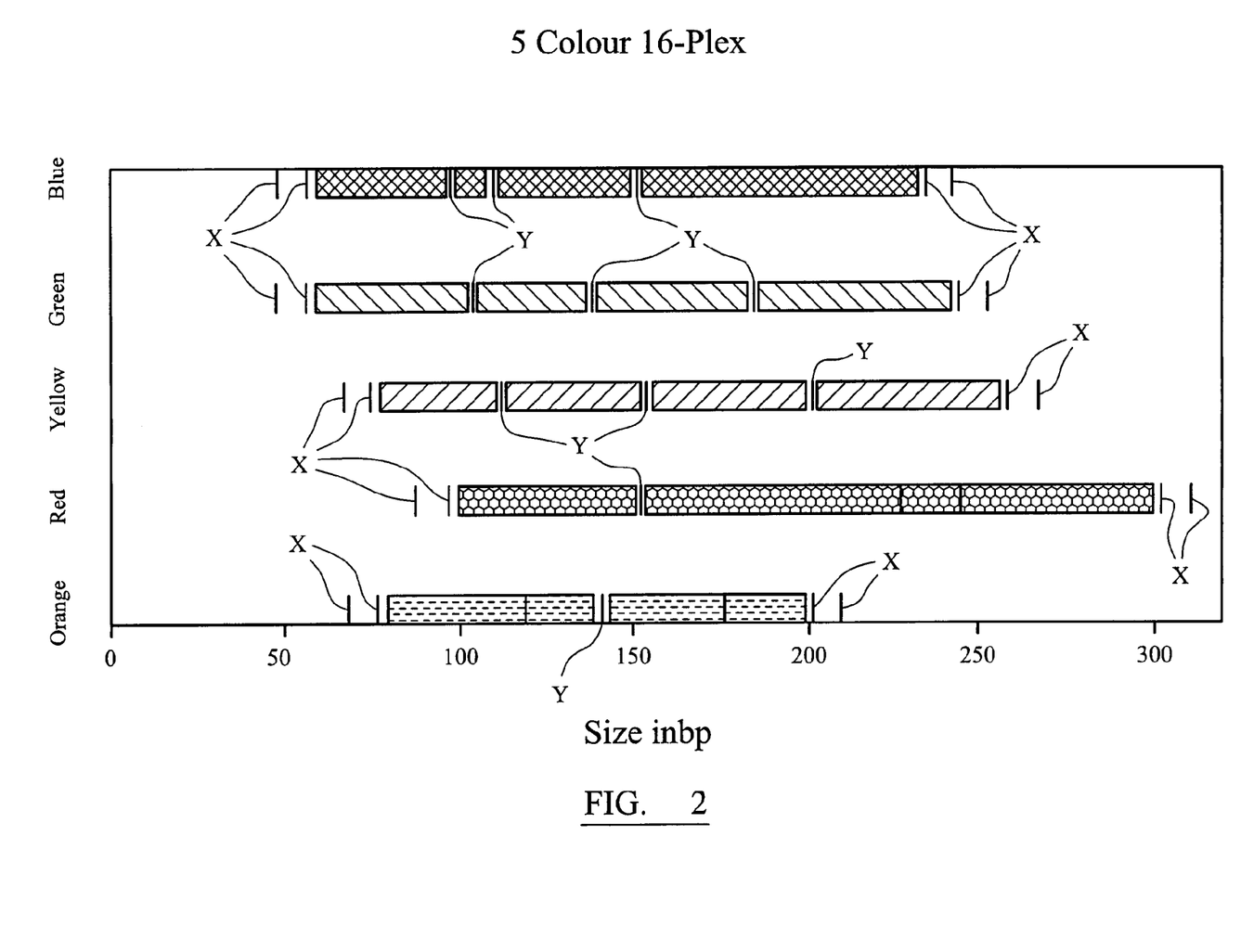
FIG. 2 is an illustration of the synthetic elements of the present invention in the context of a multiplex for the simultaneous analysis of a series of loci using five different dyes.

An example of a multiplex using the approach of the present invention is shown in FIG. 2. A multiplex enables a large number of loci to be considered simultaneously.

The blue dye (top line) is used to label loci TH01, D10 and D18. The same dye can be used for multiple loci as the range of allele sizes encountered at each of those loci is distinct from each other. Synthetic elements X are provided at the bottom and top of the overall range of these three loci at 49 and 54 base pairs and 240 and 246 base pairs. Synthetic elements Y are also provided at intermediate locations between the different loci, 100 and 154 base pairs.

The green dye (second line down) is used for loci D8, D2p, D1 and D21. Top and bottom synthetic alleles are provided at 48 and 53 base pairs and 248 and 254 base pairs. Intermediate synthetic elements are provided at 102, 140 and 186 base pairs.

The yellow dye (third line down) is used for loci D22, D16, D12 and D2q. Top and bottom synthetic elements are provided at 68 and 78 base pairs and 258 and 268 base pairs. Intermediate synthetic elements are provided at 112, 156 and 204 base pairs.

The red dye (fourth line down) is used for loci vWA, FGA and FGA rares. Top and bottom synthetic elements are provided at 88 and 96 base pairs and 302 and 310 base pairs. Intermediate synthetic elements are provided at 154 and 246 base pairs.

The orange dye (bottom line) is used for loci D3 rares, D3, D19 and D19 rares. Top and bottom synthetic elements are provided at 70 and 78 base pairs and 202 and 210 base pairs. An intermediate synthetic element is provided at 142 base pairs.

Whilst synthetic elements can be provided at the end of the range for a given loci, as shown above in FIG. 1 for a single locus and FIG. 2 for a series of loci, it would be possible to provide synthetic elements at intermediate sizes within the size range of a locus. This is possible as an alternative form or as an additional form to those described above.

Thus in the TH01 example, synthetic elements could be provided at sizes 2.2, 3.2, 5.2, 8.2, 11.2, 14.2 and 15.2. The intermediate sizes are selected so as to not correspond with any allele sizes.

Whether provided at the top and bottom of the range of alleles for a locus and/or within the range of alleles for a locus, the synthetic alleles are used in an equivalent manner to size the identities of the unknown samples.

Use of the Synthetic Alleles

The multiplex illustrated above in relation to FIG. 2, can be used as follows.

A sample which contains DNA, but for which the identities of the alleles are unknown is collected, prepared and contacted with the multiplex reagents. These reagents include the primers for amplification and the reagents for introducing the labels to the amplification products during amplification. The reagents for the different loci share common labels as per the format of FIG. 2. The reagents also include the size standard in the form of the synthetic elements previously described.

After amplification, the amplified product is split so as to introduce a part of the sample into the start of each of one or more separate capillaries provided as part of an instrument. Electrophoresis is then used to achieve the size based separation in respect of all capillaries.

After electrophoresis, the instrument and its laser inspect the capillaries to generate a data set representing the position of fluorescence and level of fluorescence observed for each capillary.

Within the data set representing the position of fluorescence and level of fluorescence observed for each capillary should be a data component for each of the synthetic elements. These are shown in FIG. 3 for the blue dye capillary, with the synthetic elements shown as the dotted line peaks.

In addition, if the analysis sample is from a single person, there should be one or two data components for each of the loci analysed corresponding to the single allele or two alleles present and observed. The presence of one or two data components will depend upon whether or not the person is heterozygous or homozygous in respect of that particular locus.

If the analysis sample is from a mixed source, then one, two or more data components will be present for each locus analysed.

As shown in FIG. 3, the person who is the sample source is homozygous for loci TH01 and D10, but is heterozygous for locus D18.

The processing of the data components is based upon the size standard. In respect of a data component corresponding to a synthetic element of the size standard, the system has knowledge as to the theoretical position of that synthetic element. This is in addition to the experimental position observed by the instrument. This is true for each synthetic element within each capillary, and hence the system has knowledge of the theoretical position of each of the synthetic elements relative to each other.

As a first step it is possible to use the theoretical positions of the synthetic elements to confirm that a capillary has functioned correctly. In particular, the consistency of migration can be checked. This may be achieved in one or more ways.

Firstly, it is possible to consider the fit between a plot of all the theoretical positions after a given migration time and a plot of the all the experimental positions after the given migration time. The fit between the plots can be considered using one or more known statistical tools for considering the goodness of fit.

Secondly, it is possible to compare the relative positions of the experimental positions against the relative positions of the theoretical positions. The extent of the two ranges may be different from one another, but the relative positions within the ranges should be consistent. This can be checked using all of the positions and comparing them and/or by selecting some of the positions and comparing from them. For instance, the theoretical position for a synthetic element can be used together with the theoretical position of the next largest synthetic element and next smallest synthetic element to establish that the theoretical position is 0.6 of the separation between the higher and lower synthetic elements. The process can then be applied to the experimental positions to see whether the 0.6 position is true in the experimental positions. The use of only some of the positions potentially allows one or more of the synthetic elements which have not migrated consistently to be identified.

If consistent migration is observed, then reliable results for the analysis sample considered in that capillary may be assumed to occur. If inconsistent migration is observed, then the results for the analysis sample may be discarded.

As a second step, the size standard can be used to determine the position of the alleles within the analysis sample. This can be achieved by establishing the position of an unknown allele in the results relative to the experimental position of one or more synthetic elements. For instance, the size standard experimental positions may be used to define a curve expressing position against size. Hence, the allele position can be compared with the plot to give an allele size. It is possible to make the comparison and determine the sizes direct from the size standard or indirectly, by using the size standard to process an allelic ladder, with the allelic ladder being used to designate the alleles in the unknown sample being analysed.

The size standard elements can be used in variety of ways. Firstly, the size standard elements associated with one locus can be used in the processing of just that locus.

Secondly, the size standard elements associated with a number of loci, by using the same characteristic unit, such as a dye colour, can be used in the processing of just those loci which use the same characteristic unit.

Thirdly, it is possible to combine the size standard elements provided with one characteristic unit in combination with the size standard elements provided with another characteristic unit. Ideally, all of the size standard elements with all of the different characteristic units would be combined. In this way, a composite size standard is achieved. Where size standard elements with one characteristic unit have a size possibly in common with or close to an allele using a different characteristic unit, the two are distinguished based upon the different characteristic units.

The comparison of the theoretical and experimental positions for one or more of the synthetic alleles can be used to ensure the plot of experimental position against size is an accurate reflection of size.

The size and its associated level of fluorescence can then be used in subsequent processing, for instance to define a genotype for the analysis sample. The genotype can be used as a search term and/or be stored in a database of genotypes In a further variation, it is possible to examine the results and see if the different alleles associated with the different dyes are migrating correctly. A cross dye calibration check is thus provided.

Figure 4:
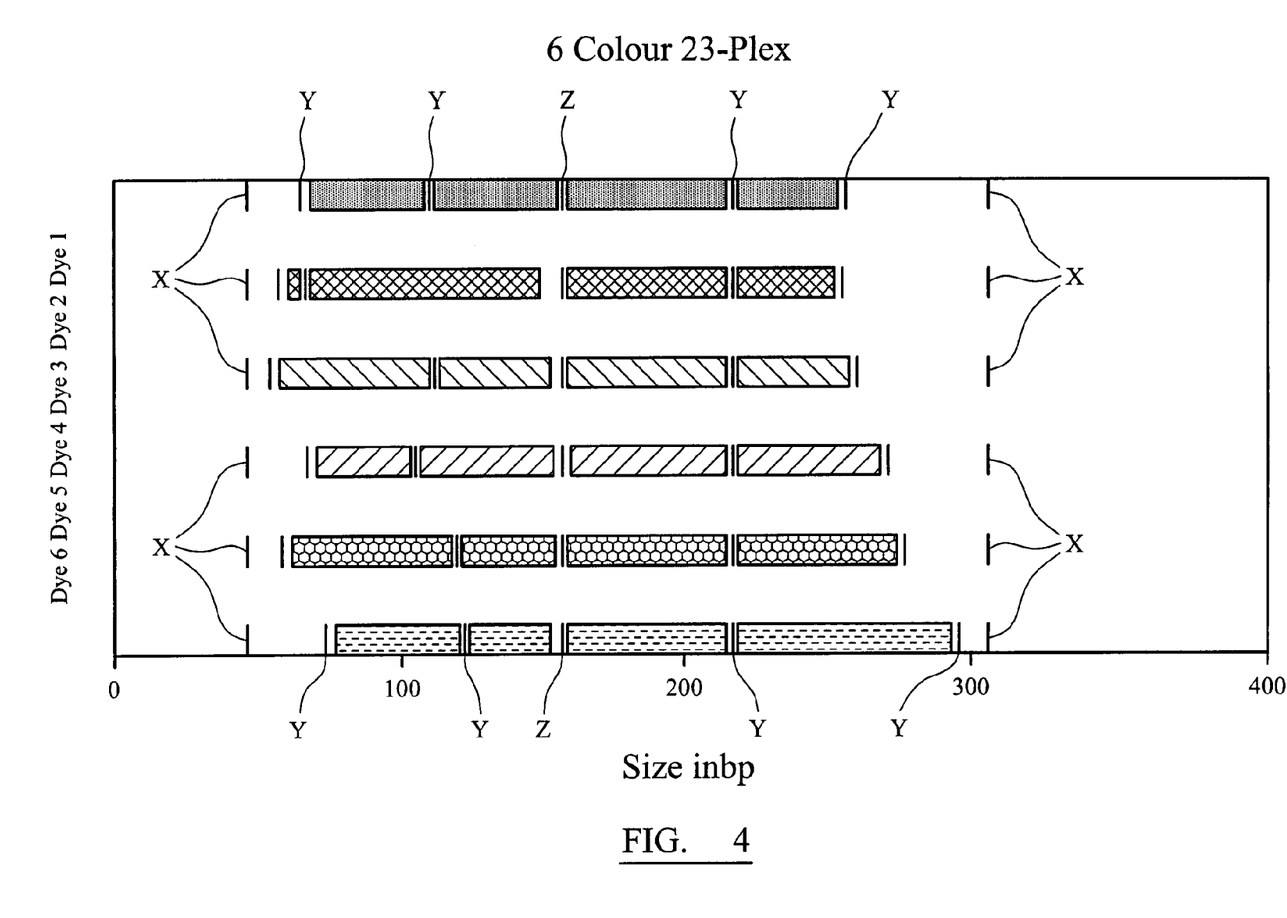
FIG. 4 is an illustration of the synthetic elements of the present invention in the context of a multiplex for the simultaneous analysis of a series of loci, using six different dyes.

To provide for this, a different example of a multiplex using the approach of the present invention is shown in FIG. 4. In this case six dyes are used.

The dark blue dye (top line) is used to label one or more loci. The same dye can be used for multiple loci where the range of allele sizes encountered at each of those loci is distinct from each other. Synthetic elements X are provided at the bottom and top of the combined loci overall range. Synthetic elements Y are also provided at intermediate locations. A synthetic element Z is provided at a common intermediate location for all of the different dyes.

The light blue dye (second line down) is used to label one or more loci. The same dye can be used for multiple loci where the range of allele sizes encountered at each of those loci is distinct from each other. Synthetic elements X are provided at the bottom and top of the combined loci overall range. Synthetic elements Y are also provided at intermediate locations. A synthetic element Z described above is provided at a common intermediate location for all of the different dyes.

The green dye (third line down) is used to label one or more loci. The same dye can be used for multiple loci where the range of allele sizes encountered at each of those loci is distinct from each other. Synthetic elements X are provided at the bottom and top of the combined loci overall range. Synthetic elements Y are also provided at intermediate locations. A synthetic element Z described above is provided at a common intermediate location for all of the different dyes.

The yellow dye (fourth line down) is used to label one or more loci. The same dye can be used for multiple loci where the range of allele sizes encountered at each of those loci is distinct from each other. Synthetic elements X are provided at the bottom and top of the combined loci overall range. Synthetic elements Y are also provided at intermediate locations. A synthetic element Z described above is provided at a common intermediate location for all of the different dyes.

The red dye (third line down) is used to label one or more loci. The same dye can be used for multiple loci where the range of allele sizes encountered at each of those loci is distinct from each other. Synthetic elements X are provided at the bottom and top of the combined loci overall range. Synthetic elements Y are also provided at intermediate locations. A synthetic element Z described above is provided at a common intermediate location for all of the different dyes.

The orange dye (bottom line) is used to label one or more loci. The same dye can be used for multiple loci where the range of allele sizes encountered at each of those loci is distinct from each other. Synthetic elements X are provided at the bottom and top of the combined loci overall range. Synthetic elements Y are also provided at intermediate locations. A synthetic element Z described above is provided at a common intermediate location for all of the different dyes.

Overall, in this embodiment, the top size synthetic elements for each dye colour are of the same size as each other and are larger in size than the largest allele of any dye colour. The lower size synthetic elements for each dye colour are also of the same size as each other and are smaller in size than the smallest allele of any dye colour. The common intermediate size synthetic elements are also of the same size as each other and are different in size from any of the alleles of any of the dye colours. As a result of the synthetic elements being the same sizes across the different dyes, those synthetic elements should migrate at the same speed and hence appear at the same position within the results.

Once verification of correct migration for the dye has been confirmed, the method may proceed on to the second step of determining the positions for the alleles.

Benefits

The provision of synthetic elements in this way provides benefits in allowing a larger number of loci to be considered using the existing number of labels. The provision of synthetic elements in this way provides for larger multiplexes to be considered in the same time frame and at the same processing costs. Larger multiplexes offer greater resolution between people and/or greater robustness to the resolution.

TABLE 1

| Locus | Alleles |
|---|---|
| VWA | 10, 11, 12, 13, 14, 15, 15.2, 16, 16.1, 17, 18, 18.1, 18.2, 18.3, 19, 19.2, 20, 21, 22, 23, 24, 25, |
| D16S539 | 4, 5, 6, 7, 8, 8.3, 9, 9.3, 10, 11, 11.3, 12, 12.1, 12.2, 13, 13.1, 13.3, 14, 14.3, 15, 16, |
| D2S1338 | 11, 12, 13, 14, 15, 16, 17, 18, 19, 19.3, 20, 21, 22, 23, 23.2, 23.3, 24, 25, 26, 27, 28, |
| D8S1179 | 7, 8, 9, 10, 10.2, 11, 12, 12.3, 13, 14, 15, 15.1, 15.3, 16, 17, 17.1, 18, 19, 20, |
| D21S11 | 12, 24, 24.2, 24.3, 25, 25.1, 25.2, 25.3, 26, 26.1, 26.2, 27, 27.1, 27.2, 27.3, 28, 28.1, 28.2, 28.3, 29, 29.1, 29.2, 29.3, 30, 30.1, 30.2, 30.3, 31, 31.1, 31.2, 31.3, 32, 32.1, 32.2, 32.3, 33, 33.1, 33.2, 33.3, 34, 34.1, 34.2, 34.3, 35, 35.1, 35.2, 35.3, 36, 36.1, 36.2, 36.3, 37, 37.2, 38, 38.2, 39, 39.2, 40.2, 41.2, |
| D18S51 | 7, 8, 9, 9.2, 10, 10.2, 11, 11.1, 11.2, 12, 12.2, 12.3, 13, 13.1, 13.2, 13.3, 14, 14.2, 15, 15.1, 15.2, 15.3, 16, 16.1, 16.2, 16.3, 17, 17.1, 17.2, 17.3, 18, 18.1, 18.2, 19, 20, 20.1, 20.2, 21, 21.1, 21.2, 22, 22.1, 22.2, 23, 23.1, 23.2, 24, 24.2, 25, 26, 27, 28.1, 28.3, 39.2, |
| D19S433 | 5.2, 6.2, 7, 8, 9, 10, 11, 11.1, 12, 12.1, 12.2, 13, 13.1, 13.2, 13.3, 14, 14.1, 14.2, 14.3, 15, 15.2, 16, 16.2, 17, 17.2, 18, 18.2, 19, 19.2, 20, |
| TH01 | 3, 4, 5, 5.3, 6, 6.1, 6.3, 7, 7.3, 8, 8.3, 9, 9.3, 10, 10.3, 11, 12, 13.3, 14, |
| FGA | 12.2, 13, 13.2, 14, 14.3, 15, 15.3, 16, 16.1, 16.2, 17, 17.1, 17.2, 18, 18.1, 19, 19.1, 19.2, 19.3, 20, 20.1, 20.2, 20.3, 21, 21.1, 21.2, 21.3, 22, 22.1, 22.2, 22.3, 23, 23.1, 23.2, 23.3, 24, 24.1, 24.2, 24.3, 25, 25.1, 25.2, 25.3, 26, 26.1, 26.2, 26.3, 27, 27.1, 27.2, 27.3, 28, 28.1, 28.2, 29, 29.1, 29.2, 30, 30.2, 31, 31.2, 32, 32.1, 32.2, 33.1, 33.2, 34.1, 34.2, 35.2, 41.1, 41.2, 42, 42.1, 42.2, 43.1, 43.2, 44, 44.2, 44.3, 45, 45.1, 45.2, 46, 46.1, 46.2, 47, 47.2, 48, 48.2, 49, 49.1, 49.2, 50.2, 50.3, 51, 52.2 |
| D3S1358 | 8, 8.3, 9, 10, 11, 12, 13, 14, 14.3, 15, 15.1, 15.2, 15.3, 16, 16.2, 17, 17.1, 17.2, 18, 18.1, 18.2, 18.3, 19, 20, |
| D10S1248 | 8, 9, 10, 11, 12, 13, 14, 15, 16, 17, 18, 19, |
| D22S1045 | 8, 9, 10, 11, 12, 13, 14, 15, 16, 17, 18, 19, 20, |
| D2S441 | 8, 9, 10, 11, 11.3, 12, 12.3, 13, 13.3, 14, 14.3, 15, 16, 17, |
| D1S1656 | 9, 10, 11, 12, 13, 13.3, 14, 14.3, 15, 15.3, 16, 16.3, 17, 17.1, 17.3, 18, 18.3, 19, 19.3, 20, 20.3, 21, |
| D12S391 | 15, 16, 17, 17.3, 18, 18.3, 19, 19.3, 20, 21, 22, 23, 24, 25, 26, |
| TPOX | 4, 5, 6, 7, 7.3, 8, 9, 10, 10.1, 10.3, 11, 12, 13, 13.1, 14, 15, 16, |
| CSF1PO | 5, 6, 6.3, 7, 7.3, 8, 8.3, 9, 9.1, 9.3, 10, 10.1, 10.2, 10.3, 11, 11.1, 11.3, 12, 12.1, 13, 14, 15, 16, |
| D5S818 | 6, 7, 8, 9, 10, 10.1, 11, 11.1, 12, 12.3, 13, 14, 15, 16, 17, 18, |
| D7S820 | 5, 5.2, 6, 6.2, 6.3, 7, 7.1, 7.3, 8, 8.1, 8.2, 8.3, 9, 9.1, 9.2, 9.3, 10, 10.1, 10.3, 11, 11.1, 11.3, 12, 12.1, 12.2, 12.3, 13, 13.1, 14, 14.1, 15, 16, |
| D13S317 | 5, 6, 7, 7.1, 8, 8.1, 9, 10, 11, 11.1, 11.3, 12, 13, 13.3, 14, 14.3, 15, 16, 17, |
| SE33 | 3, 4.2, 6.3, 7, 8, 8.1, 9, 9.2, 10, 11, 11.2, 12, 12.2, 13, 13.2, 14, 14.2, 14.3, 15, 15.2, 16, 16.2, 16.3, 17, 17.2, 17.3, 18, 18.2, 18.3, 19, 19.2, 20, 20.2, 20.3, 21, 21.1, 21.2, 22, 22.2, 23, 23.2, 24, 24.2, 25, 25.2, 26, 26.2, 27, 27.2, 28, 28.2, 29, 29.2, 30, 30.2, 31, 31.2, 32, 32.1, 32.2, 33, 33.2, 34, 34.2, 35, 35.2, 36, 36.2, 37, 38, 39, 39.2, |

The invention claim is:

1. A composition comprising a size standard and a nucleic acid sample, the size standard being to use in determining the size or sizes of two or more components in said nucleic acid sample, the components having one or more known possible sizes, the known possible sizes having a range of sizes defined by the largest and smallest known possible sizes, the range of sizes defined by the largest and smallest known possible sizes for those two or more components dose not overlap in size, the size standard including three or more size standard elements, wherein:
   a) the size of at least one of the size standard elements, is larger than the largest of the known possible sizes for the components; and
   b) the size of at least one of the size standard elements is smaller than the smallest of the known possible sizes for the components; and
   c) the size for all the size standard elements is different from any of the sizes of the known possible sizes for the components, wherein the component includes a characteristic unit, and wherein at least one of the size standard elements has a size that fits in a gap within the known possible sizes for the components and wherein the characteristic unit is used for all size or sizes of the two or more components and the same characteristic unit is used for one or more standard size elements used in determining the size or sizes of those two as more components, and wherein of the two ore more components are loci selected from the group consisting of: WVA, D16S539, D2S1338, D8S1179, D21S11, D18S51, D19S433, THOI, FGA, D3S1358, D10S1248, D22S1045, D2S441, D11 S1656, D12S391, TPOX, D14S1434, CSFIPO, D5S818, D7S820, D13S317, and SE33.

2. The composition according to claim 1, in which the size standard is for use in determining the allele size of or sizes of two or more of the loci, the loci having one or more known possible allele sizes, the known possible allele sizes having a range of sizes defined by the largest and smallest known possible size alleles, the size standard including three or more size standard elements, wherein the size of at least one of the size standard elements is larger than the largest of the known possible alleles; the size least one of the size standard elements is smaller than the smallest of the known possible alleles; and the size all of the size standard elements is different from any of the sizes of the known possible alleles.

3. The composition according to claim 1 in which at least five different components are provided which each incorporate a different characteristic unit from each other.

4. The composition according to claim 1 in which one or more of the size standard elements are of a size which is less than the smallest size of the known possible sizes for one locus and greater than the largest size of the known possible iszes of another loeus.

5. The composition according to claim 4 in which the smallest size of the one locus is greater in size than the largest size of another locus.

6. The composition according to claim 1 in which one or more of the size standard elements are of a size which is less than one of the known possible sizes for a locus and is greater than one of the known possible sizes of the locus.

7. The composition according to claim 1, in which
a) a size standard element is provided which is at least 1 base pair smaller in size than the smallest known possible alleles of the two or more components the size standard is being used to size; and/or
b) a size standard elements is provided which is at least 1 base pair larger in size than the largest known possible alleles of the two or more components the size standard is being used to size; and/or
c) a size standard element is provided intermediate the range of known possible alleles for one locus and the known possible size range for another locus, where the sizes of the different loci are distinguishable as a loci with smaller sizes and a loci with larger sizes, and the size standard element is provided to be at least 1 pair larger in size than the largest allele of the range with the smaller sizes at least 1 base pair in size than the smallest allele of the range with the larger sizes.

8. The composition according to claim 1 in which
a) a size standard element is provide which is at least 4 pairs smaller than the smallest known possible alleles of the two or more components the size standard is being used to size; and/or
b) a size standard element is provided which is at least 4 base larger in size than the largest known possible alleles of the two or more components the size standard is being used to size; and/or
c) a size standard element is provided intermediate the size range of known possible alleles for one locus and the known possible size range for another locus, wherein the size of the different loci are distinguishable as loci with smaller sizes and a loci with larger sizes, and the size standard element is provided to be at least 4 base pairs larger in size than the largest allele of the range with the smaller sizes and at least 4 base pairs smaller in size than the smallest allele of the range with the larger sizes.

9. A kit, the kit comprising: a size standard, the size standard including the size standard being for use in determining sizes of two or more components in a nucleic acid sample, the components having one or more known possible sizes, the known possible sizes having a range of sizes defined by the largest and smallest known possible size, the size standard including three or more size standard elements, wherein a) the size of at least one of the size standard elements is larger than largest of the known possible sizes for the components; b) the size of at least one of the standard elements is smaller than the smallest of the known possible sizes for the components; and c) the size of at least one of the size standard elements is different from any of the sizes of the known possible sizes for the components, wherein at least one of the size standard element has a size that fits in a gap within the known possible sizes for a locus; the kit further comprising one or more of the following components: the kit further comprising one or more of the following components;
a) one or more primers;
b) one or more probes;
c) one or more characteristic units;
d) one or more buffers;
e) one or more HCI solutions;
f) one or more EDTA solutions;
g) one or more gender markers;
h) one or more allelic ladders;
i) one or more enzymes;
J) one or more reagents for use in PCR;
k) one or more deoxynucleotide triphosphates;
l) one or more solutions containing Mg and/or Mn ions; and
m) one more solution containing K ions,
wherein the components includes a characteristic unit, and wherein the characteristic unit is used for all sizes or sizes of the components and the same characteristic unit is used for the standard size elements used in determining the size or sizes of the two or more components, and wherein the components are loci selected from the group consisting of: VWA, D16S539, D2S1338, D8S1179, D21S11, D18551, D19S433, THOI, FGA, D3S1358, DIOS1248, D22S1045, D2S441, DIS1656, D12S391, TPOX, D14S1434, CSFIPO, D5S5818, D7S820, D13S317 and SE33.

10. A method of analyzing a nucleic acid sample to determine the size or sizes of two or more component of the sample, the components having one or more known possible sizes, the known possible sizes having a range defined by the largest and smallest known possible sizes, the method comprising:
a) introducing a size standard to at least a part of the sample, the size standard comprising three or more size standard elements;
b) performing a size based separation on at least a part of the samples,
c) determining the positions of the size standard elements detected; and
d) using the size standard elements to determine the size or sizes of the components;
wherein:
i) the size of at least one of the size standard elements is larger than the largest of the known possible sizes for the components;
ii) the size of at least one of the size standard elements is smaller than the smallest of the known possible sizes for the components; and
iii) the size of at least one of the size standard elements is different from any of the sizes of the known possible sizes for the components,
wherein at least one of the size standard elements has a size that fits in a gap within the known possible sizes for a locus,
wherein the component includes a characteristic unit, and wherein the characteristic unit is used for all size or sizes of the two or more components and the same characteristic unit is used for the standard size elements used in determining the size or sizes of the component, and wherein the components are loci selected from the group consisting of: VWA, 0165539, 0251338, 0851179, 021511, 018551, 0195433, THOI, FGA, 0351358, 01051248, 02251045, 025441, 0151656, 0125391, TPOX, 01451434, C5FIPO, 055818, 075820, 0135317 and 5E33.

* * * * *